US011458816B2

(12) United States Patent
Baker et al.

(10) Patent No.: US 11,458,816 B2
(45) Date of Patent: Oct. 4, 2022

(54) SELF CLEANING OF RIDE SHARING VEHICLE

(71) Applicant: Honda Motor Co., Ltd., Tokyo (JP)

(72) Inventors: Alex W. Baker, Ostrander, OH (US); Michael A. Baumbarger, Marysville, OH (US); Jacob J. Olchovy, Marysville, OH (US); Kimberly R. Araki, Bellefontaine, OH (US); Zainab I. Ali, Marysville, OH (US)

(73) Assignee: HONDA MOTOR CO., LTD., Tokyo (JP)

(*) Notice: Subject to any disclaimer, the term of this patent is extended or adjusted under 35 U.S.C. 154(b) by 78 days.

(21) Appl. No.: 16/671,987

(22) Filed: Nov. 1, 2019

(65) Prior Publication Data

US 2021/0129632 A1    May 6, 2021

(51) Int. Cl.
*B60H 3/00* (2006.01)
*A61L 2/02* (2006.01)
(Continued)

(52) U.S. Cl.
CPC .............. *B60H 3/0078* (2013.01); *A61L 2/02* (2013.01); *A61L 2/26* (2013.01); *A61L 9/22* (2013.01); *B01D 46/0032* (2013.01); *B60S 1/64* (2013.01); *A61L 2202/11* (2013.01); *A61L 2202/14* (2013.01); *A61L 2202/25* (2013.01); *A61L 2209/11* (2013.01); *A61L 2209/14* (2013.01);
(Continued)

(58) Field of Classification Search
CPC ........... A61L 2/02; A61L 9/22; B60H 3/0078; B01D 46/0032; B60S 1/64
See application file for complete search history.

(56) References Cited

U.S. PATENT DOCUMENTS 4,806,204 A    2/1989  Manfré et al.
5,433,772 A *  7/1995  Sikora ................. B03C 3/32
                                                  422/120
(Continued)

FOREIGN PATENT DOCUMENTS

CN    201515714     6/2010
CN    101817291 A   9/2010
(Continued)

OTHER PUBLICATIONS

D. Bial, D. Kern, F. Alt, and A. Schmidt. "Enhancing outdoor navigation systems through vibrotactile feedback", CHI '11 Extended Abstracts on Human Factors in Computing Systems, Vancouver, BC, Canada, May 7-12, 2011 pp. 1273-1278. https://dl.acm.org/citation.cfm?doid=1979742.1979760.

(Continued)

*Primary Examiner* — Kevin Joyner
(74) *Attorney, Agent, or Firm* — Rankin, Hill & Clark LLP

(57) ABSTRACT

A system for cleaning a compartment includes a conductive thread incorporated near a surface that has microbes on it. An electric current may flow through the conductive thread to kill the microbes on the surface through low-frequency electromagnetic pulse sterilization of the surface. The conductive trace is also in contact with air in the compartment. The electric current flowing through the conductive trace also ionizes the air within the compartment, which produces charged particles that are removed from the air.

9 Claims, 4 Drawing Sheets

(51) Int. Cl.
   *A61L 9/22* (2006.01)
   *B01D 46/00* (2022.01)
   *B60S 1/64* (2006.01)
   *A61L 2/26* (2006.01)
   *B60R 13/02* (2006.01)
   *B60L 53/00* (2019.01)
   *B60N 2/70* (2006.01)

(52) U.S. Cl.
   CPC ...... *B01D 2279/40* (2013.01); *B01D 2279/65* (2013.01); *B60L 53/00* (2019.02); *B60N 2/70* (2013.01); *B60R 13/0243* (2013.01)

(56) References Cited

U.S. PATENT DOCUMENTS

| | | | |
|---|---|---|---|
| 5,624,132 | A | 4/1997 | Blackburn et al. |
| 5,678,854 | A | 10/1997 | Meister et al. |
| 5,971,432 | A | 10/1999 | Gagnon et al. |
| 5,996,807 | A | 12/1999 | Rumpf et al. |
| 6,478,858 | B2 | 11/2002 | Angermann et al. |
| 6,543,299 | B2 | 4/2003 | Taylor |
| 6,613,227 | B2 | 9/2003 | Rickie |
| 6,697,723 | B2 | 2/2004 | Olsen et al. |
| 6,964,370 | B1 | 11/2005 | Hagale et al. |
| 7,880,613 | B1 | 2/2011 | Maeng |
| 8,060,282 | B2 | 11/2011 | Breed |
| 8,729,505 | B2 | 5/2014 | Seibt |
| 9,631,589 | B2 | 4/2017 | Harp |
| 9,772,422 | B2 | 9/2017 | Hull et al. |
| 10,000,097 | B2 | 6/2018 | Kim et al. |
| 10,274,647 | B2 | 4/2019 | Seder et al. |
| 2001/0015131 | A1 | 8/2001 | Angermann et al. |
| 2003/0122669 | A1 | 7/2003 | Filippov et al. |
| 2003/0132156 | A1 | 7/2003 | Rickle |
| 2010/0160882 | A1 | 6/2010 | Lowe |
| 2011/0116967 | A1* | 5/2011 | Roy .............. H05H 1/2406 422/22 |
| 2011/0221459 | A1 | 9/2011 | Uno et al. |
| 2011/0240751 | A1 | 10/2011 | Rauh et al. |
| 2014/0102984 | A1 | 4/2014 | Harp |
| 2014/0134387 | A1 | 5/2014 | Yamada et al. |
| 2014/0210603 | A1 | 7/2014 | Walser |
| 2015/0329041 | A1 | 11/2015 | Salter et al. |
| 2016/0010273 | A1 | 1/2016 | Ashayer-Soltani et al. |
| 2016/0278444 | A1 | 9/2016 | Jordan et al. |
| 2016/0379466 | A1 | 12/2016 | Payant et al. |
| 2018/0005766 | A1 | 1/2018 | Fairbanks et al. |
| 2018/0225988 | A1 | 8/2018 | Morgado |
| 2018/0307315 | A1 | 10/2018 | Gong et al. |
| 2018/0333756 | A1 | 11/2018 | Seder et al. |

FOREIGN PATENT DOCUMENTS

| | | |
|---|---|---|
| CN | 201624172 | 11/2010 |
| CN | 104389076 B | 3/2015 |
| CN | 205417544 U | 8/2016 |
| CN | 205462733 U | 8/2016 |
| CN | 106149134 A | 11/2016 |
| CN | 108032711 | 5/2018 |
| CN | 207523509 U | 6/2018 |
| CN | 207568736 U | 7/2018 |
| CN | 207583526 U | 7/2018 |
| CN | 208730904 U | 4/2019 |
| DE | 102008064006 | 10/2009 |
| DE | 102010023892 | 8/2011 |
| DE | 102014005403 A1 | 10/2014 |
| EP | 2163459 | 3/2010 |
| EP | 3287304 | 2/2018 |
| JP | 2013154667 | 8/2013 |
| KR | 20030026458 A | 4/2003 |
| KR | 101557245 | 10/2015 |
| KR | 101590557 B1 | 2/2016 |
| KR | 20170111499 A | 10/2017 |
| KR | 20180019459 | 2/2018 |
| WO | WO2007004000 A1 | 1/2007 |
| WO | WO2018031476 | 2/2018 |

OTHER PUBLICATIONS

F. Kiss, R. Boldt, B. Pfleging, and S. Schneegass. "Navigation Systems for Motorcyclists: Exploring WearableTactile Feedback for Route Guidance in the Real Worid", CHI 2018, Apr. 21-26, 2018, Montréal, QC, Canada. http://www.medien.ifi.lmu.de/pubdb/publications/pub/kiss2018motorcyclenavi/kiss2018motorcyclenavi.pdf.

F .A. Olsen. "Killing bacteria with electromagnetic fields". DTU Chemical Engineering. Jun. 23, 2017. https://www.kt.dtu.dk/english/about-us/news/2017/06/killing-bacteria-with-electromagnetic-fields1?id=a6007cba-7469-4a20-a339-f17c96a82424, Printed Feb. 11, 2020.

Nippon Tungsten Co., Ltd., "Ionized Wire for Air Cleaner", https://www.nittan.co.jp/en/tech/techinfo/ionized.html.

Notice of Allowance of U.S. Appl. No. 16/672,012 dated Jan. 27, 2021, 5 pages.

Office Action of U.S. Appl. No. 16/672,036 dated Jul. 8, 2021, 39 pages.

T. Dias, and R. Monaragal. "Development and analysis of novel electroluminescent yarns and fabrics for localized automotive interior illumination", SAGE Journals, vol. 82 issue: 11, pp. 1164-1176, Jan. 19, 2012. https://journals.sagepub.com/doi/abs/10.1177/0040517511420763?journalCode=trjc.

Office Action of U.S. Appl. No. 16/672,012 dated Oct. 6, 2020, 20 pages.

Office Action of U.S. Appl. No. 16/672,036 dated Nov. 12, 2021, 27 pages.

Notice of Allowance of U.S. Appl. No. 16/672,036 dated Feb. 22, 2022, 21 pages.

* cited by examiner

```
┌─────────────────────────────────────────┐
│  CAUSING ELECTRIC CURRENT TO FLOW       │
│  THROUGH A CONDUCTIVE THREAD WITHIN     │
│  THE COMPARTMENT TO THEREBY CREATE AN   │──58
│  ELECTROMAGNETIC FIELD THAT IS PULSED   │
│  AT A FREQUENCY THAT KILLS MICROBES     │
│  WITHIN THE VEHICLE                     │
└─────────────────────────────────────────┘
                    │
                    ▼
┌─────────────────────────────────────────┐
│  CAUSING ELECTRIC CURRENT TO FLOW       │
│  THROUGH THE CONDUCTIVE THREAD TO       │──60
│  CREATE GAS IONS WITHIN THE COMPARTMENT │
└─────────────────────────────────────────┘
                    │
                    ▼
┌─────────────────────────────────────────┐
│  MOVING AIR THAT IS WITHIN THE          │
│  COMPARTMENT SO THAT THE GAS IONS       │
│  ADHERE TO AIRBORNE PARTICLES IN THE    │──62
│  AIR, THEREBY FORMING CHARGED AIRBORNE  │
│  PARTICLES                              │
└─────────────────────────────────────────┘
                    │
                    ▼
┌─────────────────────────────────────────┐
│  REMOVING THE CHARGED AIRBORNE          │──64
│  PARTICLES FROM THE AIR                 │
└─────────────────────────────────────────┘
```

FIG. 5

SELF CLEANING OF RIDE SHARING VEHICLE

BACKGROUND

Certain obstacles exist for full adoption of ride sharing vehicles by the public. One of these obstacles is cleanliness of the vehicle. Autonomous ride-sharing vehicles will expose passengers to germs in the air within the vehicle and on surfaces that have been touched by previous passengers. The air and surfaces must be cleaned by the owner of the vehicle, which may take the vehicle out of service for some time during cleaning.

BRIEF DESCRIPTION

According to one aspect, a method of cleaning a compartment includes causing electric current to flow through a conductive thread within the compartment to thereby create an electromagnetic field that is pulsed at a frequency within the compartment.

According to another aspect, a method of cleaning a compartment includes causing electric current to flow through a conductive thread within the compartment to thereby create an electromagnetic field that is pulsed at a frequency that kills microbes within the compartment. The electric current is caused to flow through the conductive thread to create gas ions within the compartment. Air that is within the compartment is moved so that that the gas ions adhere to airborne particles in the air, thereby forming charged airborne particles. The charged airborne particles are then removed from the air.

According to another aspect, a system for cleaning a compartment includes a conductive thread arranged in an interior of the compartment and having electric current flowing therethrough. The electric current flowing through the conductive thread creates an electromagnetic field that is pulsed at a frequency within the compartment.

According to another aspect, a system for cleaning a compartment includes a conductive thread, a ventilation system, and a filter. The conductive thread is arranged in an interior of the compartment and has electric current flowing therethrough. The ventilation system is in communication with the interior and moves air that is within the compartment. The air is circulated by the ventilation system through the filter. The electric current flowing through the conductive thread creates an electromagnetic field that is pulsed at a frequency that kills microbes within the compartment. The electric current flowing through the conductive thread creates gas ions that adhere to airborne particles in the air, thereby forming charged airborne particles. The filter includes an electrode that attracts the charged airborne particles to thereby remove the charged airborne particles from the air.

BRIEF DESCRIPTION OF THE DRAWINGS

FIG. 5 is a schematic block diagram illustrating a method according to the present subject matter.

DETAILED DESCRIPTION

Figure 1:
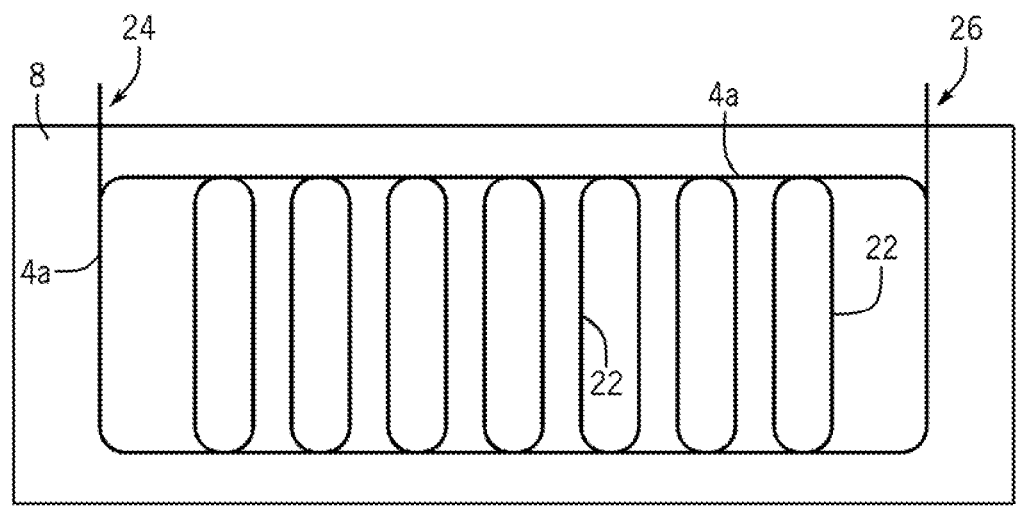
FIG. 1 is a plan view of a material layer including a conductive thread according to the present subject matter.

Ride-sharing vehicles, especially autonomous ride-sharing vehicles, may accumulate germs and other microbes in the air within the vehicle and on surfaces of the interior compartment from contact with passengers or other sources. Further, the air inside these vehicles may include airborne particulates that pollute the air within the vehicle. These microbes and particulates may pose a threat to the health of an occupant of the vehicle. In order to sanitize/clean a compartment, especially a passenger compartment of an electric autonomous ride-sharing vehicle, the present subject matter provides a system that kills various microbes on surfaces and removes particulates from the air within the compartment. The process for cleaning the vehicle may be performed while the vehicle power source is being recharged by an external power source, and thus the vehicle does not have to be removed from service exclusively for cleaning.

With reference to the figures, the system 2 for cleaning/sanitizing a compartment 6 includes a conductive thread 4 arranged in the compartment 6. The conductive thread 4 has an electric current flowing through it. A first conductive thread 4a may be arranged in a material layer 8 and a second conductive thread 4b may be arranged in a filter medium 10. When electric current is flowed through the first conductive thread 4a, a resonance is created in microbes within the interior of the compartment 6, e.g. microbes on a surface 12 in the interior of the compartment 6. The resonance is at such a frequency that kills the microbes, thus sanitizing the surface 12. When electric current is flowed through the second conductive thread 4b, gas ions are created, which join with particulates in the air within the compartment to form charged airborne particles. These charged airborne particles are removed from the air by an electrode 14, thus cleaning the air in the compartment 6.

The system may be employed for cleaning any compartment 6, such as a passenger compartment 6 of a vehicle 16 or other compartments 6 like storage compartments, boxes, rooms, or storage bins for example. However, the invention will be discussed in more detail herein with respect to the system 2 being used for cleaning a passenger compartment 6 of the vehicle 16.

The vehicle 16 is not particularly limited, and may include a vehicle powered by electricity or petroleum products (e.g. gasoline or diesel fuel). The vehicle 16 may include a ride-sharing vehicle, which is a vehicle that is typically owned by one entity (e.g. person), yet used by other entities (e.g. other persons). The ride-sharing vehicle may include taxis, trains, buses, and autonomous ride-sharing vehicles, for example. The vehicle 16 may be an autonomous vehicle, or a user-operated vehicle.

When the system 2 is employed in a ride-sharing vehicle 16, e.g. an electric powered autonomous ride-sharing vehicle, the cleaning/sanitizing may proceed when passengers are outside of the passenger compartment 6 of the vehicle 16. This sanitizing may occur during a period where an occupant is not using the vehicle 16 for transport, and it is confirmed that no occupants are in the passenger compartment of the vehicle 16. Confirmation that there are no occupants in the passenger compartment 6 may be accomplished utilizing, for example, cameras, pressure sensors on the vehicle seats 28, through portable electronic devices associated with an occupant, or other sensing mechanisms that are able to confirm the passenger compartment 6 is devoid of occupants.

In the case of an electric vehicle 16, such cleaning operation may occur during a charging cycle for a rechargeable power source 18 (e.g. rechargeable battery) of the vehicle 16, such as when the vehicle power source 18 is connected to an external power source 20 for charging the vehicle power source 18. The external power source 20, the vehicle power source 18, or a combination thereof may supply the electric current flowing through the conductive thread 4. The benefit of sanitizing during charging of the vehicle power source 18 is that the energy necessary to perform the cleaning operation may come from the external power source 20, and may therefore not inhibit any other vehicle capabilities that may draw power from the vehicle power source 18 and may be required during normal operation of the vehicle 16 for transport of an occupant.

One or both of the power sources 18, 20 are in electrical communication (wired or wirelessly) with the conductive thread 4 for supplying the electric current to the conductive thread 4.

The vehicle power source 18 may include a battery or alternator of the vehicle 16. The external power source 20 may include a battery, a generator, a photoelectric cell, a municipal power source, or other source of the electric current.

Figure 2:
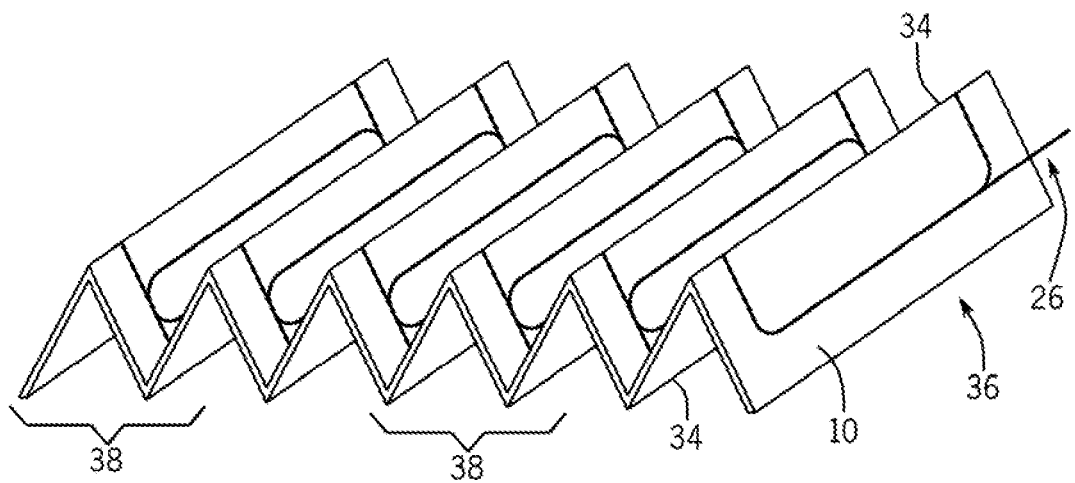
FIG. 2 is a perspective view of a filter medium including a conductive thread in a folded state according to the present subject matter.

The first conductive thread 4a may be incorporated into the material layer 8 for including in the interior of the compartment 6 of the vehicle 16, and the second conductive thread 4b may be included in a filter 32 as a stand-alone structure (FIG. 3) or incorporated into a filter medium 10 (FIG. 2) of the filter 32. FIG. 2 depicts the second conductive thread 4b incorporated into a filter medium 10, however this is not required and the second conductive thread 4b can be incorporated into the filter 32 separate from the filter medium 10.

The conductive thread 4 is an elongated conductive material arranged on the material layer 8 or on the filter medium 10. The conductive thread 4 is not particularly limited, and may include any one or more known conductive threads, including but not limited to a printed and cured conductive ink, a conductive polymer impregnated in or coated on a thread, a thin flexible conductive metal wire or braided cable, etc., or combinations thereof.

The conductive thread 4 may be arranged in or on the material layer 8 or the filter medium 10, for example by printing, adhesive application, or other techniques, and/or may be arranged within or inside the material layer 8 or filter medium 10 (e.g. under an outer surface), for example by weaving, sewing, knitting, injection, mechanical mixing or other techniques.

The material layer 8 may be a flexible sheet-like structure capable of covering a portion of the compartment 6, e.g. covering various components in the vehicle 16. The material layer 8 including the first conductive thread 4a may be flexible. The material layer 8 may include a woven or non-woven textile, synthetic or natural leather, polymers; filter medium, etc., or combinations thereof.

The filter medium 10 may be included in the filter 32 for screening out impurities in the air. The filter medium 10 is not particularly limited, and may include any material that screens out impurities from a fluid (e.g. air in the compartment 6), including but not limited to fibrous or porous material including paper, cotton, and spun fiberglass; woven and nonwoven textiles; polymers such as foamed polymers; screens or mesh such as stainless steel mesh; etc.

In a non-limiting embodiment (FIG. 2), the filter medium 10 is a flexible sheet-like structure, e.g. filter paper. The filter medium 10 along with the second conductive thread 4b, which is also flexible and thus may be bent or folded without a loss of continuity, may be folded/pleated along fold lines 34 in alternating directions to form a zig-zag shaped structure 36 including one or more Z-folds 38. The filter medium 10 and second conductive thread 4b may be arranged in other configurations, including for example, tri-folds, gate folds, double parallel folds, rolling, bending, etc.

The zig-zag shaped structure 36, which includes the second conductive thread 4b and filter medium 10, may be arranged in a self-contained housing 40 in the shape of a box, to provide a cartridge construction to the filter 32. However, this is not required and the filter medium 10 and conductive thread 4 may be used without a housing 40. The filter 32 may include electrical contacts 42 on the external surface of the housing 40 for making an electrical connection with the vehicle power source 18 or external power source 20 so that electric current is supplied to the second conductive thread 4b. The vehicle 16 may include corresponding electrical contacts 44 that are in electrical communication with one or both of the power sources 18, 20 and are for mating with, and electrically connecting with, the electrical contacts 42 of the filter 32 for allowing the transfer of electric current from the power sources 18, 20 to the second conductive thread 4b.

Figure 4:
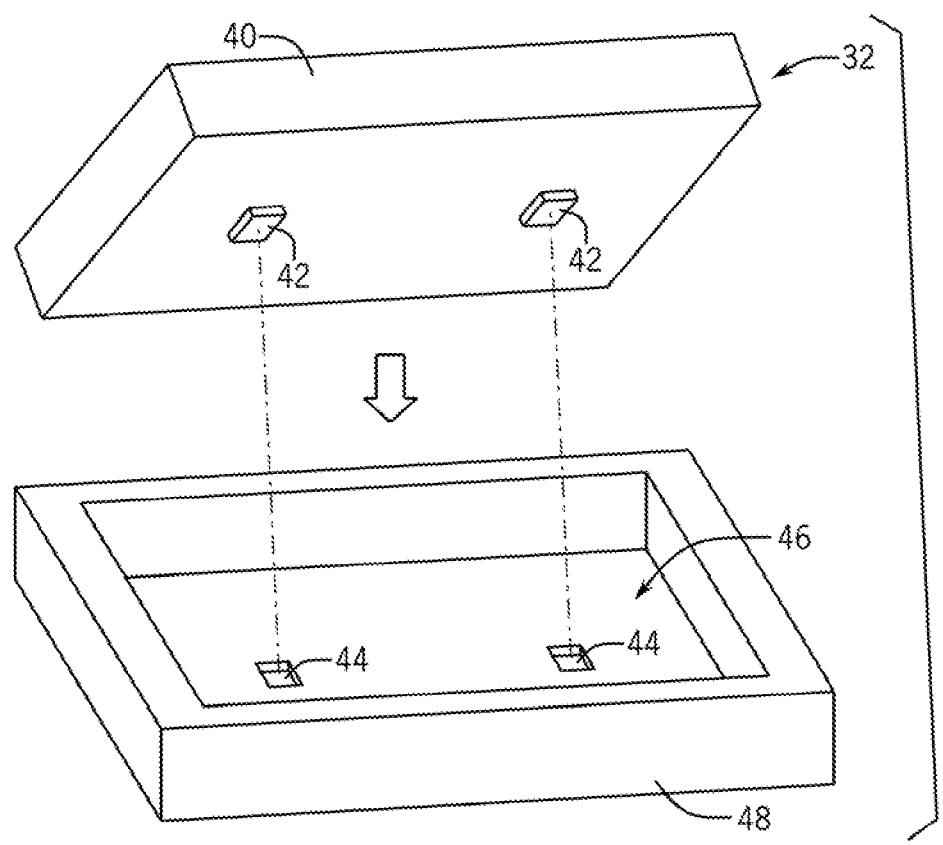
FIG. 4 is a perspective view of arranging a filter on a vehicle according to the present subject matter.

The electrical connection between the contacts 42, 44 may be formed by their mutual alignment during mounting of the filter 32 on the vehicle 16. With reference to FIG. 4, electrical contacts 44 of the vehicle 16 are arranged in an interior 46 of an air filter box 48. The interior 46 has a size and shape (e.g. rectangle) that correspond to the size and shape of the filter 32. The electrical connection is made between the contacts 42, 44 by inserting the filter 32 in the interior 46 of the air filter box 48, thereby bringing the electrical contacts 42 on the filter 32 into contact with the electrical contacts 42 in the air filter box 48 as shown. Electrical communication with the second conductive thread 4b may be made by other means.

The material layer 8 or filter 32 may include one or more conductive threads 4, and the conductive thread 4 may be arranged in a regular pattern or randomly thereon. The conductive thread 4 may be arranged in a grid-like pattern, or may be arranged in other regular patterns.

As depicted in FIG. 1, the first conductive thread 4a is arranged in a regular pattern including one or more coils 22. Each coil 22 may include one or more turns of the conductive thread 4. By including the coils 22, electric current flowing through the coils 22 may produce a magnetic field by induction. In this embodiment, the conductive thread 4 may be flexible, so that after the material layer 8 is applied over a vehicle component, the conductive thread 4 maintains its electrical continuity from one end 24 to the other end 26 so that the electric current from the power source 18 can flow through the conductive thread 4 from the one end 24 to the other end 26.

The material layer 8 may be arranged to cover various objects including vehicle components such as the seat 28, arm rest 30, door lining 68, floor, or other components of the vehicle 16 that may be contaminated with microbes. The material layer 8 may define the surface 12, which is touched by occupants of the vehicle 16 and has microbes thereon. Alternatively, the material layer 8 may not define the surface 12, and instead may be arranged under another layer that defines the surface 12, or may be arranged at a location within the vehicle 16 that is remote from the surface 12.

Figure 3:
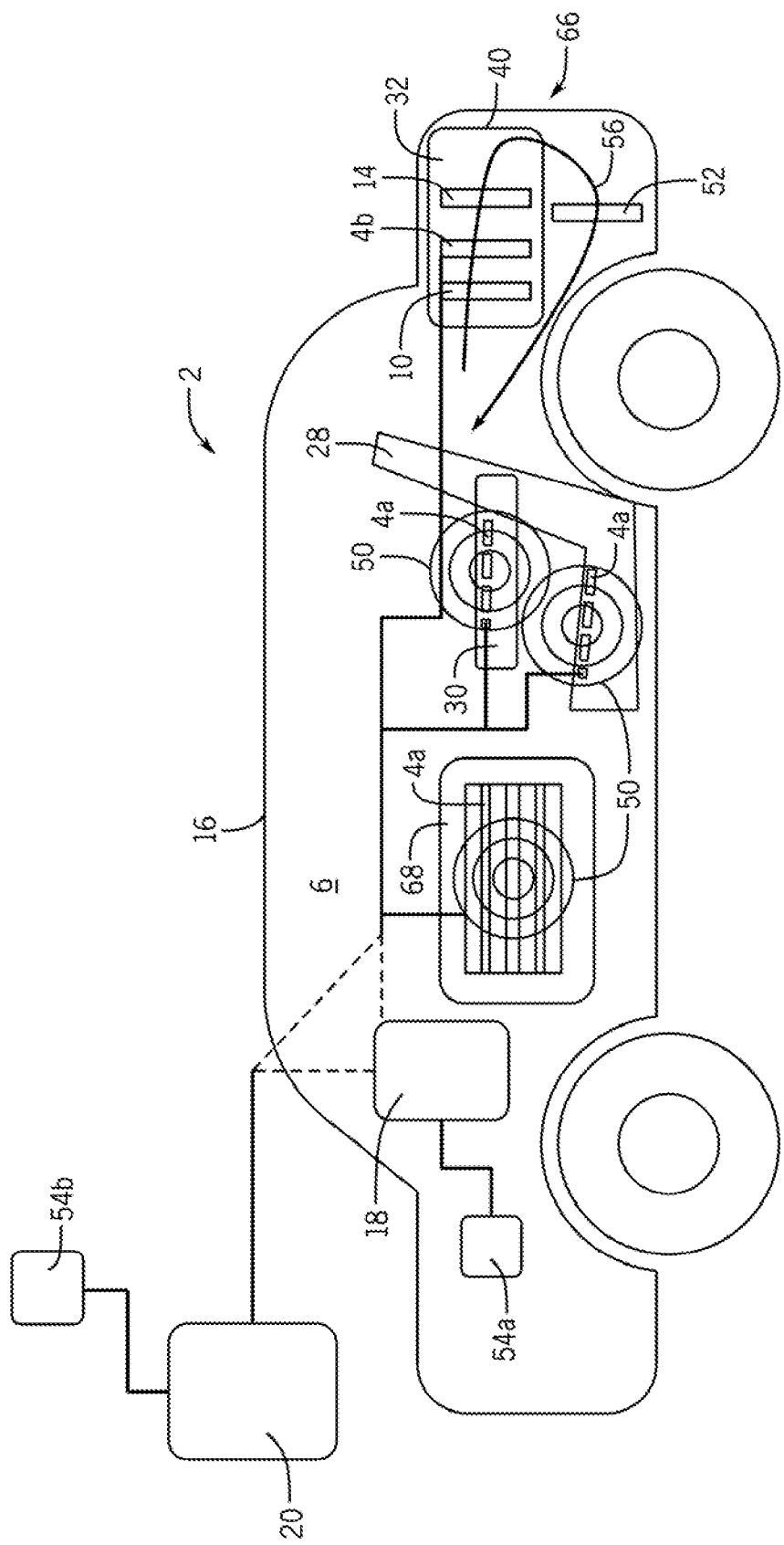
FIG. 3 is a schematic cross-sectional view of a system for cleaning a compartment according to the present subject matter.

More than one conductive thread 4 and material layers 8 may be arranged in different locations within the vehicle 16 as depicted in FIG. 3. These multiple first conductive threads 4a may have electrical current passing through them simultaneously, sequentially, or otherwise.

The electric current flowing through the first conductive thread 4a creates an electromagnetic field 50, which may be pulsed at a resonant frequency that pairs with the natural resonant frequency of microbes within the passenger compartment 6 of the vehicle 16. The pulse frequency of the electromagnetic field 50 may cause the microbes to resonate at a frequency that destroys or kills the microbes. The pulse frequency of the electromagnetic field 50 may be varied over a frequency range as part of a "frequency sweep" in which a plurality of different frequencies are used, which frequencies may pair with the resonant frequencies of various kinds or sizes of microbes to kill or destroy the various kinds or sizes of microbes. Multiple frequency sweeps may be performed during a cleaning cycle.

The second conductive thread 4b may be arranged other than as shown in a series of coils 22, and may instead be arranged so as to be connected to a series of resistors, capacitors, and/or diodes (not shown) is a Cockroft-Walton Ladder Network. The electric current flowing through the second conductive thread 4b may ionize air by creating gas ions. These gas ions may adhere to airborne particles in the air, thereby forming charged airborne particles. The electrode 14 in the filter 32 may attract these charged airborne particles and remove them from the air. The air in the passenger compartment may be circulated through the filter 32 by a fan 52 included along with the filter 32 as part of a ventilation system 66 of the vehicle 16. The circulated air 56 may be moved by operation of the fan 52 through the filter 32.

The circulated air 56 may enter the filter 32 and larger airborne particles in the circulated air 56, which are non-charged airborne particles, may be removed from the circulated air 56 by the filter medium 10. Thereafter, the circulated air 56 may pass by the second conductive thread 4b, which has electric current flowing therethrough and is thereby producing gas ions. The gas ions attach to finer airborne particles in the circulated air 56 to form charged airborne particles. The circulated air 56, including the charged airborne particles, is then moved by the ventilation system 66 past the electrode 14, which attracts the charged airborne particles and removes them from the circulated air 56. The circulated air 56 is then recirculated as clean air back into the passenger compartment 6 of the vehicle 16.

The first and second conductive threads 4a, 4b may be operated individually or together as desired in order to sanitize/clean the compartment 6. For example, the first conductive thread 4a may have electric current flowing therethrough, while the second conductive thread 4b does not have electric current flowing therethrough, or vice versa. Alternatively, the first and second conductive threads 4a, 4b may both have electric current flowing therethrough at the same time.

The system 2 may include an electronic control unit (ECU) 54 that is used to control a delivery (e.g. the flow) of the electric current from the power source 18, 20 to the conductive thread 4. The ECU may be a vehicle ECU 54a for controlling the vehicle power source 18, or the ECU may be an external ECU 54c for controlling the external power source 20. The ECU is configured to control the power source 18, 20 to provide the electric current to the conductive thread 4 at a certain level, timing, frequency, duration, etc. in order to clean the compartment 6 as desired. The ECU 54 may be programmed to operate automatically, or may be manually controlled by a switch.

With reference to FIG. 5 a method of cleaning a compartment 6 (e.g. a passenger compartment of a vehicle 16) includes at 58, causing electric current to flow through a conductive thread 4 (e.g. first conductive thread 4a) within the compartment 6 to thereby create an electromagnetic field 50 that is pulsed at a frequency, e.g. a frequency that kills microbes within the compartment 6 (i.e. "low-frequency electromagnetic pulse sterilization"). The microbes that are killed are those in the compartment 6 that resonate with the electromagnetic field 50. These microbes may be on the surface 12 of a vehicle component. The method may stop there, or may further include at 60, causing electric current to flow through the conductive thread 4 (e.g. second conductive thread 4b) to create gas ions within the compartment. The creation of the gas ions may occur in the filter 32 of the vehicle 16 as electric current is flowing through the second conductive thread 4b, and may also occur as electric current is flowing through the first conductive thread 4a outside the filter 32. At 62, the method includes moving air that is within the compartment 6 so that that the gas ions adhere to airborne particles in the air, thereby forming charged airborne particles. The air may be moved through the ventilation system 66, and by operation of the fan 52 of the ventilation system 66. The fan 52 may also cause movement of air within the compartment 6, and not necessarily cause the air to move through the ventilation system 66. For this purpose, the electrode 14 may be arranged outside the ventilation system 66, for example within the compartment 6. At 64, the charged airborne particles are removed from the air. The electrode 14 is electrified so as to be charged opposite from the charged particles so as to attract the charged particles to itself. The charged particles adhere to the electrode 14 and thus are removed from the air, which is then recirculated back into the compartment 6.

The method of cleaning the vehicle 16 (the cleaning cycle) may occur during a charging cycle when the vehicle power source 18 is being recharged. The external power source 20 may be used to recharge the vehicle power source 18. Because the cleaning cycle involves a flow of electric current through the conductive thread 4 in a low-frequency electromagnetic pulse sterilization, the cleaning cycle may be performed when no occupants are within the passenger compartment 6.

Another method of cleaning the vehicle 16 may include locking doors of the vehicle 16 to prevent entry into the passenger compartment 6, and charging the vehicle power source 18 in a charging cycle. Current is passed through the conductive thread as part of a frequency sweep with the components containing the conductive thread, to thereby operate at a frequency, e.g. a frequency that kills the desired microbe (e.g. bacteria/germs). Multiple sweeps may occur at one or more frequencies. The method may end there, or optionally following the frequency sweep, electric current is flowed through the conductive thread 4 at a power necessary for the conductive thread 4 to ionize the air for purification. A ventilation system (e.g. a HVAC system) may be used to force air across the conductive thread to as to allow particles in the air to be charged, in addition to routing the air through a filter medium 10.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently

The invention claimed is:

1. A system for cleaning a compartment, comprising:
   the compartment,
   a vehicle component in an interior of the compartment,
   a material layer covering the vehicle component, and
   a conductive thread arranged in the material layer and having electric current flowing therethrough;
   wherein the electric current flowing through the conductive thread creates an electromagnetic field that is pulsed at a frequency within the compartment so as to create a resonance frequency in microbes within the compartment that kills the microbes;
   wherein the compartment is a passenger compartment of an electric vehicle; and
   wherein the vehicle component includes a seat, an arm rest, or a door lining.

2. The system according to claim 1, wherein the electric current is provided by a power source in electrical communication with the conductive thread.

3. The system according to claim 2, further including the power source.

4. The system according to claim 3, further including a control unit in communication with the power source and controlling a delivery of the electric current to the conductive thread.

5. The system according to claim 2, wherein the power source is external to the system.

6. The system according to claim 1, wherein the electromagnetic field is pulsed at a plurality of frequencies so as to create resonance frequencies in various kinds or various sizes of the microbes that kill the microbes.

7. The system according to claim 1, wherein:
   the system further comprises the compartment, a ventilation system in communication with the interior and moving air that is within the compartment, and a filter through which the air is circulated by the ventilation system;
   the filter further includes a second conductive thread having electric current flowing therethrough;
   the electric current flowing through the second conductive thread creates gas ions that adhere to airborne particles in the air, thereby forming charged airborne particles; and
   the filter includes an electrode that attracts the charged airborne particles to thereby remove the charged airborne particles from the air.

8. The system according to claim 7, wherein:
   the ventilation system includes a fan moving the air;
   the filter further includes filter medium removing non-charged airborne particles from the air; and
   the second conductive thread is arranged in the filter medium.

9. A system for cleaning a compartment, comprising:
   the compartment,
   a conductive thread arranged in an interior of the compartment and having electric current flowing therethrough,
   a ventilation system in communication with the interior and including a fan moving air that is within the compartment, and
   a filter through which the air is circulated by the ventilation system, the filter including filter medium removing non-charged airborne particles from the air, an electrode, and a second conductive thread arranged in the filter medium and having electric current flowing therethrough,
   wherein the electric current flowing through the conductive thread creates an electromagnetic field that is pulsed at a frequency within the compartment so as to create a resonance frequency in microbes within the compartment that kills the microbes;
   wherein the electric current flowing through the second conductive thread creates gas ions that adhere to airborne particles in the air, thereby forming charged airborne particles; and
   wherein the electrode attracts the charged airborne particles to thereby remove the charged airborne particles from the air.

* * * * *